US 9,372,166 B2

(12) United States Patent
Daamen et al.

(10) Patent No.: US 9,372,166 B2
(45) Date of Patent: Jun. 21, 2016

(54) INTEGRATED CIRCUIT COMPRISING A THERMAL CONDUCTIVITY BASED GAS SENSOR

(71) Applicant: ams International AG, Rapperswil-Jona (CH)

(72) Inventors: Roel Daamen, Herkenbosch (NL); Aurelie Humbert, Brussels (BE); Pascal Bancken, Opwijk (BE)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 318 days.

(21) Appl. No.: 14/047,137

(22) Filed: Oct. 7, 2013

(65) Prior Publication Data
US 2014/0102172 A1 Apr. 17, 2014

(30) Foreign Application Priority Data
Oct. 12, 2012 (EP) .................................... 12188372

(51) Int. Cl.
*G01N 27/18* (2006.01)
*G01N 27/12* (2006.01)
*G01N 27/22* (2006.01)
G01N 25/56 (2006.01)
G01N 33/00 (2006.01)

(52) U.S. Cl.
CPC .............. *G01N 27/18* (2013.01); *G01N 27/223* (2013.01); *G01N 25/56* (2013.01); *G01N 33/0032* (2013.01)

(58) Field of Classification Search
CPC .... G01N 25/56; G01N 27/18; G01N 33/0032
See application file for complete search history.

(56) References Cited

U.S. PATENT DOCUMENTS

| 7,114,848 B2 * | 10/2006 | Kaneko | ................ G01N 27/048 374/109 |
| 7,243,541 B1 * | 7/2007 | Bey | ........................ G01D 3/022 73/431 |
| 7,832,269 B2 * | 11/2010 | Bey, Jr. | ................... G01D 21/02 73/29.02 |

(Continued)

FOREIGN PATENT DOCUMENTS

CN 102081070 A 6/2011
CN 102405524 A 4/2012

(Continued)

OTHER PUBLICATIONS

Briand, D., J. Courbat, and N. F. de Rooij. "Autonomous sensors on flexible foils powered by RFID and energy scavenging for environmental and goods monitoring." Proceedings of PowerMEMS (2008).*

(Continued)

*Primary Examiner* — Lisa Caputo
*Assistant Examiner* — Punam Roy
(74) *Attorney, Agent, or Firm* — McDermott Will & Emery LLP

(57) ABSTRACT

An integrated circuit and a method of making the same. The integrated circuit includes a semiconductor substrate. The integrated circuit also includes a relative humidity sensor on the substrate. The relative humidity sensor includes a first sensor electrode, a second sensor electrode, and a humidity sensitive layer covering the first and second electrodes. The integrated circuit further includes a thermal conductivity based gas sensor on the substrate. The thermal conductivity based gas sensor has an electrically resistive sensor element located above the humidity sensitive layer.

13 Claims, 16 Drawing Sheets

(56) References Cited

U.S. PATENT DOCUMENTS

| | | | | |
|---|---|---|---|---|
| 7,842,544 | B2* | 11/2010 | Smeys | H01L 21/4853 257/E21.499 |
| 8,476,084 | B1* | 7/2013 | Yang | H01L 25/16 257/E21.502 |
| 8,507,955 | B2* | 8/2013 | Cummins | G01N 27/121 257/252 |
| 8,652,961 | B1* | 2/2014 | Yang | H01L 21/8221 257/415 |
| 8,823,007 | B2* | 9/2014 | Yang | B81C 1/00246 257/204 |
| 9,103,705 | B2* | 8/2015 | Bilic | G01D 1/00 |
| 2005/0247107 | A1* | 11/2005 | Speldrich | G01N 25/60 73/29.01 |
| 2008/0315333 | A1 | 12/2008 | Combi et al. | |
| 2009/0308155 | A1* | 12/2009 | Zhang | G01N 27/223 73/335.02 |
| 2010/0116024 | A1* | 5/2010 | De Coulon | G01N 33/006 73/25.03 |
| 2011/0226041 | A1 | 9/2011 | Cummins | |
| 2012/0244655 | A1 | 9/2012 | Moore et al. | |
| 2013/0256825 | A1* | 10/2013 | Humbert | H01L 27/16 257/467 |

FOREIGN PATENT DOCUMENTS

| | | |
|---|---|---|
| EP | 2 420 826 A1 | 2/2012 |
| JP | 2004-037180 A | 2/2004 |

OTHER PUBLICATIONS

Oprea, A., et al. "Temperature, humidity and gas sensors integrated on plastic foil for low power applications." Sensors and Actuators B: Chemical 140.1 (2009): 227-232.*

Alexandru Oprea, Nicolae Bârsan, Udo Weimar, Marie-Luise Bauersfeld, Dirk Ebling, Jürgen Wöllenstein. "Capacitive humidity sensors on flexible RFID labels." Sensors and Actuators B: Chemical, vol. 132, Issue 2, Jun. 16, 2008, pp. 404-410.*

Abad, Estefania, et al. "Flexible tag microlab development: gas sensors integration in RFID flexible tags for food logistic." Sensors and Actuators B: Chemical 127.1 (2007): 2-7.*

Gay, N.; Fischer, W., "Ultra-low-power RFID-based sensor mote," in Sensors, 2010 IEEE pp. 1293-1298, Nov. 1-4, 2010.*

Roozeboom, C.L.; Hong, V.A.; Ahn, C.H.; Ng, E.J.; Yang, Y.; Hill, B.E.; Hopcroft, M.A.; Pruitt, B.L., "Multifunctional integrated sensor in A 2×2 mm epitaxial sealed chip operating in a wireless sensor node," in Micro Electro Mechanical Systems (MEMS), 2014 IEEE 27th International Conference on, pp. 773-776, Jan. 26-30, 2014.*

Roozeboom, C.L.; Sim, J.Y.; Wickeraad, D.; Dura, B.; Smith, W.S.; Hopcroft, M.A.; Hartwell, P.G.; Williams, R.S.; Pruitt, B.L., "Multifunctional integrated sensors for the environment," in Micro Electro Mechanical Systems (MEMS), 2012 IEEE 25th International Conference on, pp. 144-147, Jan. 29, 2012-Feb. 2, 2012.*

Zampolli, Stefano, et al; "Ultra-low-power components for an RFID Tag with physical and chemical sensors"; Microsyst Technol 14, Springer-Verlag; 8 pages (Nov. 11, 2007).

Cozir Technology; "The world's lowest power NDIR Carbon dioxide Sensor"; Datasheet, retrieved from the Internet Jul. 23, 2012; 1 page.

Elektronik; EE891 Series datasheet; retrieved from the Internet Jul. 23, 2012; 2 pages.

Barrettino, "CMOS Hotplate Chemical Microsensors Series: Mcirotechnology and MEMS"; Chapter 4: Microhotplate in CMOS technology 2007.

Nurashikin, Nordin, et al; "Micro-hotplate based temperature stabilization system for CMOS SAW resonators"; Microsyst Technol 15, Springer-Verlag; 7 pages (Feb. 10, 2009).

European Search Report for application No. 12188372.2 dated Apr. 3, 2013.

* cited by examiner

INTEGRATED CIRCUIT COMPRISING A THERMAL CONDUCTIVITY BASED GAS SENSOR

CROSS-REFERENCE TO RELATED APPLICATIONS

This application claims the priority under 35 U.S.C. §119 of European patent application no. 12188372.2, filed on Oct. 12, 2012, the contents of which are incorporated by reference herein.

BACKGROUND OF THE INVENTION

This invention relates to an integrated circuit. In particular, this invention relates to an integrated circuit comprising a thermal conductivity based gas sensor.

Nowadays, integrated circuits may comprise a plethora of different sensors, such as ambient light (AL) sensors, temperature (T) sensors, gas sensors, relative humidity (RH) sensors, specific analyte detection sensors, and so on.

Integrated circuits of this kind have a wide range of applications. For example, they can be used in the field of supply chain management to track and monitor the freshness of food and beverages. They can also be used as environmental sensors, for example as part of a heating, ventilation and air conditioning (HVAC) system in an automobile or in a building (e.g. a Smart Building). Additional applications include those in agricultural (e.g. the sensing of environmental conditions in greenhouses) or in medical fields. Their provision in mobile communications devices such as mobile telephones, tablets or laptops can also enable a wide range of further applications that require measurements of local environmental factors.

The provision of sensors in integrated circuits of this kind allows devices to be produced that have a small form factor. For example, due to their small form factor, integrated circuits incorporating one or more sensors can be included in Radio Frequency Identification (RFID) tags, allowing for easy programming and readout.

Moreover, it allows large numbers of sensors to be manufactured cheaply, using established semiconductor processing techniques.

One kind of sensor that can be implemented in an integrated circuit is a thermal conductivity based gas sensor. These operate by passing a current through an electrically resistive sensor element, which causes the sensor element to heat up. The heat that is generated is dissipated by the surrounding environment including the substrate of the integrated circuit and also by any gas that is present in the vicinity of the sensor element. The resistivity of the sensor element is proportional to its temperature, and the temperature of the sensor element is in turn sensitive to the thermal conductivity of the gas (which governs the rate at which the gas can conduct heat away from the sensor element). Since the thermal conductivity of the gas is determined by its density and composition, it follows that electrical resistance measurements of the sensor element can therefore provide information about the gas. Since different gases have different thermal conductivities, the sensor can in principal be used to determine the presence and composition of a gas.

Thermal conductivity based gas sensors of this kind are known to be affected by cross sensitivity to relative humidity and ambient temperature. In order to correct for these factors, it is customary to provide a separate relative humidity sensor and temperature sensor. Optimally, these additional sensors would be provided in close proximity to the gas sensor. However, integration of such a diverse range of sensors on a single substrate is difficult. Accordingly, the additional sensors are typically provided on a separate substrate and/or in a separate package.

Another issue affecting thermal conductivity based gas sensors of this kind is the fact they operate at relatively high temperatures (which can be as high as 300° C.). Dissipation of heat into the substrate is problematic in the sense that it can cause unwanted heating of the other components in the integrated circuit, and also increases the amount of power needed to operate the sensor.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided an integrated circuit. The integrated circuit includes a semiconductor substrate. The integrated circuit also includes a relative humidity sensor on the substrate. The relative humidity sensor includes a first sensor electrode, a second sensor electrode, and a humidity sensitive layer covering the first and second electrodes. The integrated circuit further includes a thermal conductivity based gas sensor on the substrate. The thermal conductivity based gas sensor has an electrically resistive sensor element located above the humidity sensitive layer.

According to another aspect of the invention, there is provided a method of making an integrated circuit. The method includes providing a semiconductor substrate. The method also includes forming a relative humidity sensor on the substrate by forming a first sensor electrode and a second sensor electrode, and then depositing a humidity sensitive layer to cover the first and second electrodes. The method further includes forming a thermal conductivity based gas sensor on the substrate by forming an electrically resistive sensor element above the humidity sensitive layer of the relative humidity sensor.

Embodiments of this invention allow a relative humidity sensor and a thermal conductivity based gas sensor to be integrated on the same semiconductor substrate. In use, the relative humidity sensor can be used to correct for cross sensitivity of the thermal conductivity based gas sensor to relative humidity levels in the gas to be detected. Since the relative humidity sensor and a thermal conductivity based gas sensor are provided on the same substrate, they can be located in closer proximity to each other than can be achieved were the sensors to be provided on separate substrates and/or in different packages. This can improve the accuracy of the cross-sensitivity corrections that are made.

Locating the electrically resistive sensor element of the thermal conductivity based gas sensor above the humidity sensitive layer can limit thermal losses to the substrate. Accordingly, lower power operation can be enabled. In some examples, the material used for the humidity sensitive layer can be chosen to have a low thermal conductivity, thereby further limiting these thermal losses.

It is noted that for the purposes of this application, the term "humidity" refers to the presence individual water molecules. These molecules may, for example, be carried in air. These water molecules do not constitute water vapour as such, since they are not condensed into droplets of water.

In some examples, the electrically resistive sensor element can be located on an upper surface of the humidity sensitive layer. The humidity sensitive layer can thereby provide mechanical support for the sensor element. In an alternative embodiment, the electrically resistive sensor element can be suspended above an upper surface of the humidity sensitive layer. This arrangement can increase the effective surface area of sensor element (since an underside of the sensor element becomes exposed to the target gas), which can increase the sensitivity of the sensor. Additionally, released configuration of the sensor element can further limit thermal loses to the substrate.

In one embodiment, vias can be provided that pass through the humidity sensitive layer. These vias can contain electrically conductive material connecting to the electrically resistive sensor element of the thermal conductivity based gas sensor. This compact arrangement allows the sensor element to be connected to other features of the integrated circuit (e.g. control and read-out circuitry). The electrically conductive material may only partially fill the vias. For example it may coat the sidewalls of the vias. In some examples, the material in the vias may be the same material as that used for the sensor element of the thermal conductivity based gas sensor. This can allow the material forming the sensor element and the material for filing the vias to be laid down in a common process step.

In some examples, a metallization stack can be provided on a major surface of the substrate. As is known in the art of integrated circuit manufacture, a metallization stack can typically comprise a plurality of dielectric layers including patterned metal features that allow various components of the integrated circuit to be interconnected. The layers in the stack containing the patterned metal features can be separated by dielectric layer containing vias that interconnect the patterned metal features. An upper layer of the metallization stack can include metal features for receiving connections from the relative humidity and gas sensors. It is noted that the term "upper layer" does not necessarily refer specifically to a topmost layer of the stack. For example, an upper layer may be any layer in the top half of the stack.

A passivation stack can be provided on the metallization stack. Passivation stacks are known in the art of integrated circuit manufacture for providing mechanically and chemical protection (e.g. against scratching or corrosion) for the metallization stack.

The relative humidity sensor and the thermal conductivity based gas sensor can both be located above the passivation stack. Accordingly, electrically resistive elements and electrodes thereof can be formed using back-end-or-line (BEOL) processes. Moreover, this configuration allows the sensors to be provided in the same integrated circuit as other features such as CMOS transistors, that are interconnected by the metallization stack and that can form features such as control circuitry for the sensors.

Vias can be provided that pass through the passivation stack. These vias can be filled with electrically conductive material connecting to at least one of the electrically resistive sensor element and the first and second sensor electrodes of the relative humidity sensor. Electrical connections can thereby be made between the sensors and the aforementioned metal features in an upper layer of the metallization stack.

An opening can be provided through the humidity sensitive layer and the passivation stack for providing access to a bond pad in the metallization stack. This can allow electrical connection to be made to the integrated circuit in a manner that does not adversely affect the operation of the sensors.

The thermal conductivity based gas sensor can be located adjacent the relative humidity sensor on the substrate. By "adjacent" it is meant that no other features such as other sensors, circuitry or components are located in between the gas sensor and the humidity sensor. The close proximity of the sensors in this arrangement allows for a high degree of accuracy when correcting for cross sensitivity of the gas sensor to humidity.

The electrically resistive sensor element of the thermal conductivity based gas sensor can extend in a plane parallel to a major surface of the substrate. This can allow the sensor element to be formed in a substantial planar configuration, which in turn can allow the element to be laid down using standard metallization techniques in a BEOL process.

The integrated circuit can include additional sensors, to allow multi-mode sensing. One of these additional sensors can be a temperature sensor. The temperature sensor can be used to correct for cross sensitivity of the gas sensor to ambient temperature. At least one further sensor can also be provided, extending the multi-modal sensing functionality of the integrated circuit. Examples of such additional sensors include ambient light sensors, gas sensors configured to sense different target gases, pressure sensors, flow sensors, accelerometers, orientation sensors, magnetometers, and infra-red (or near infra-red) based proximity sensors.

According to a further aspect of the invention, there is provided a Radio Frequency Identification (RFID) tag comprising an integrated circuit of the kind described above.

According to another aspect of the invention, there is provided a mobile communications device comprising an integrated circuit of the kind described above.

According to a further aspect of the invention, there is provided a heating, ventilation and air conditioning (HVAC) system comprising one or more integrated circuits of the kind described above.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

As described herein, embodiments of this invention can provide an integrated circuit that comprises a relative humidity sensor and a thermal conductivity based gas sensor located on a common semiconductor substrate. The integration of these two different kinds of sensor on the same substrate allows them to be placed in close proximity to each other. Corrections applied to the output of the thermal conductivity based gas sensor to correct for relative humidity levels (as measured by the relative humidity sensor) can thereby be applied more accurately than for alternative solutions in which a relative humidity sensor is provided off-chip.

An additional benefit provided by embodiments of the invention arises due to the fact that the electrically resistive sensor element is located above a humidity sensitive layer. The humidity sensitive layer, which can in some embodiments provide mechanical support for the (often delicate) electrically resistive sensor element, can also act to inhibit dissipation of heat generated during operation, into the substrate. Thermal losses to the substrate may therefore be limited, allowing the device to be operated at lower power.

Integration of disparate kinds of environmental sensor into a common semiconductor substrate is a distinctly non-trivial matter, complicated by numerous considerations including: compatibility of the various materials used with existing semiconductor manufacturing processes, mechanical and chemical (e.g. robustness against mechanical shock or corrosion) stability, and thermal budget. Additionally, there are considerations of process integration using semiconductor techniques that do not depart significantly from the standard techniques used in device manufacture (whereby the costs associated with adding sensors of this kind to integrated circuits do not become prohibitive).

Figure 1:
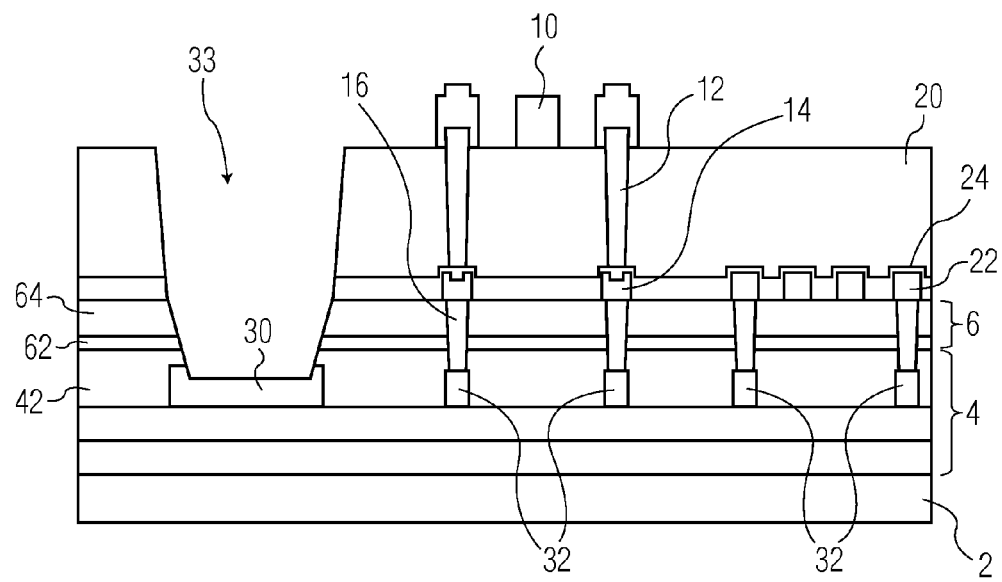
FIG. 1 shows a cross section of an integrated circuit according to an embodiment of the invention.

A first example of an integrated circuit according to an embodiment of the invention is illustrated in FIG. 1.

The integrated circuit comprises a semiconductor substrate 2. The substrate may, for example, be a silicon substrate, however in principle alternative types of substrate could also be used. In some examples, the substrate 2 can comprise components such as transistors and other circuitry to support operation of the sensors described herein and/or any further features (such as further sensors) that are provided on the substrate. The circuitry can, for example, include features such as control logic, read-out circuitry, an analogue to digital converter (ADC) for converting sensor readings into the digital domain, and memory for storing data collected by the sensors. In principle, these features can be implemented using standard devices and circuitry and for this reason they will not be elaborated upon further herein.

In the present example, the integrated circuit includes a metallization stack 4. Metallization stacks are known in the art of semiconductor device manufacture and generally include one or more layers of patterned metal features that are separated by dielectric. The patterned metal features of a metallization stack typically provide interconnections for the various components and devices provided in the substrate 2.

In the present example, the metallization stack 4 includes a series of layers as illustrated in FIG. 1. These layers can include an upper layer 42. The upper layer 42 includes a bond pad 30, which allows for connection to the substrate 2 and the various devices therein. The upper layer 42 also includes a series of metal features 32 which, as explained below, allow for interconnection of the relative humidity sensor and the thermal conductivity based gas sensor to components (e.g. control circuitry) located in the substrate 2.

As shown in FIG. 1, the present example further includes a passivation stack 6. Passivation stacks are known in the art for providing a protective layer over metallization stacks, to prevent the incursion of unwanted materials (such as water) into the stack or the underlying substrate 2, and for providing a degree of mechanical protection (e.g. scratch protection) for the metallization stack. In the present example, the passivation stack 6 can include one or more layers 62 of high density plasma oxide (HDP oxide) 62, and a layer of $Si_3N_4$ 64 above the HDP oxide layer(s) 62.

In FIG. 1 it can be seen that vias 16, which are filled with electrically conductive material (e.g. aluminium, tungsten, an AlCu alloy, or some other BEOL process compatible material), pass through the passivation stack 6. These vias 16 provide connections through the passivation stack between the metal features 32 in the upper layer 42 the metallization stack 4 and sensors as described in further detail below.

According to an embodiment of the invention, both the relative humidity sensor and the thermal conductivity based gas sensor can be provided above the passivation stack of an integrated circuit. This can allow the sensors to be manufactured using standard back end of line (BEOL) processing techniques including the use of metallic features for constructing parts of the sensors such as the electrically resistive sensor element of the gas sensor or the sensor electrodes of the relative humidity sensor. In this way, the features of the sensors of the integrated circuit can conveniently be manufactured in a manner that does not significantly affect the construction of the various other features and components that are provided within the substrate 2 itself.

In the present example, the integrated circuit includes a relative humidity sensor that comprises a pair of sensor electrodes 22. These sensor electrodes can, for example, comprise a metal such as aluminium or tungsten, or some other BEOL process compatible material. The pair of sensor electrodes 22 in the present example are located directly on an upper surface of the passivation stack 6. In alternative examples, one or more intermediate layers may be present. To increase their surface area while increasing their proximity to each other, the pair of sensor electrodes 22 may be configured as a pair of interdigitated electrodes (FIG. 1 shows this configuration in cross section), as is well known in the art. Alternative configurations, such as a simple pair of parallel capacitor plates could also be used.

The sensor electrodes 22 of the relative humidity sensor in this example are covered with an optional anticorrosion layer 24. This anticorrosion layer can, for example, comprise a material such as $Ta_2O_5$, although any suitable anticorrosion protective layer could be employed.

The integrated circuit further comprises a humidity sensitive layer 20. This humidity sensitive layer 20 is provided over the sensor electrodes 22. In the present example, the humidity sensitive layer 20 comprises polyimide. Other suitable materials include $Al_2O_3$, polyimide, $TiO_2$, $SiO_2$, polyesters, PMMA (Polymethyl methacrylate), BCB (Benzocyclobutene), polysulfates, cellulose acetate butyrate, and porous silicon.

During operation, water molecules from the surrounding environment (e.g. carried in the target gas) enter the humidity sensitive layer 20. The presence of the water molecules in the humidity sensitive layer 20 alters the dielectric constant of the humidity sensitive layer 20. This change in the dielectric constant can be measured as a change in capacitance between the pair of electrodes 22 of the relative humidity sensor. Accordingly, ambient levels of humidity can be monitored. As described herein, these measurements of humidity levels can be used to correct for the cross-sensitivity to humidity of the thermal conductivity based gas sensor described below.

The integrated circuit in this example further includes a thermal conductivity based gas sensor. The gas sensor includes an electrically resistive sensor element 10. The electrically resistive sensor element 10 is located above the humidity sensitive layer 20. In the present example, the electrically resistive sensor element 10 is located on an upper surface of the humidity sensitive layer 20. The humidity sensitive layer 20 thereby provides mechanical support for the sensor element 10.

The electrically resistive sensor element 10 in the present example is connected by vias 12 filled with electrically conductive material (e.g. aluminium, tungsten, an AlCu alloy, or some other BEOL process compatible material) to the metal features 14 provided on the upper surface passivation stack 6. As described above, the metal filled vias 16 in turn provide connection to the metal features 32 in the metallization stack 4. In this way, the electrically resistive sensor element 10 of the thermal conductivity based gas sensor can be connected to other features such as the control circuitry and read out circuitry that can be provided in the substrate 2.

The electrically resistive sensor element 10 can comprise an elongate metal line. For example, this metal line may be provided in a meander configuration, to increase the surface area of the line while maintaining a relatively compact construction. Suitable materials for the electrically resistive sensor element include Al, W, TiW(N), Cu, or Cu covered with e-less materials such as CoWB or WoWP. Conveniently, these materials are compatible with existing BEOL processes.

In use, the thermal conductivity based gas sensor operates by passing a current through the electrically resistive sensor element 10. This causes the sensor element 10 to heat up. The heat that is generated is dissipated by the surrounding environment. Some of the heat will be dissipated through the humidity sensitive layer 20 into the passivation stack, metallization stack 4 and substrate 2. In some examples, the material used for the humidity sensitive layer 20 can be selected to have a relatively low thermal conductivity, thereby limiting such losses to the substrate. Polyimide constitutes one such example material. At least some of the heat generated in the sensor element 10 during operation will be dissipated by a gas that is present in the vicinity of the integrated circuit. As described above, the rate at which such as gas can carry heat away from the sensor element 10 is governed by the composition and concentration of the gas. It follows that electrical resistance measurements of the sensor element 10 can provide information about the gas that is present.

The integrated circuit in the present example further includes an opening 33 through the humidity sensor layer 20 and the passivation stack 6 to expose a bond pad 30. This allows electrical connection to be made to the integrated circuit using, for example, wire bonding processes. Any number of such bond pads 30 and respective openings can be provided, in accordance with design requirements.

Figure 2:
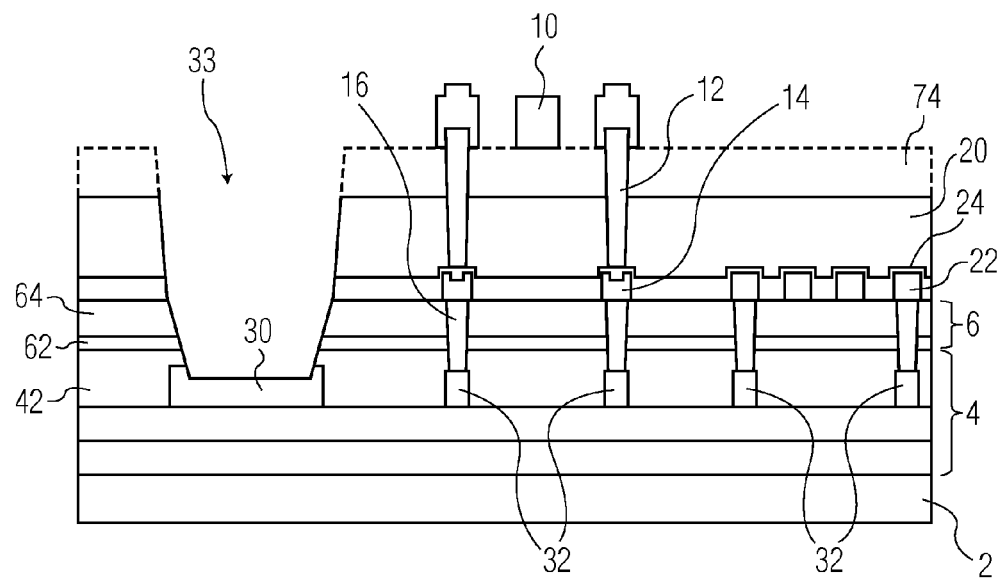
FIG. 2 shows a cross section of an integrated circuit according to another embodiment of the invention.

A second embodiment of the invention is illustrated in FIG. 2. The embodiment of FIG. 2 is substantially similar to that described above in relation to FIG. 1, with the exception that the electrically resistive sensor element 10 of the thermal conductivity based gas sensor is not located directly on an upper surface of the humidity sensitive layer 20. Instead, the sensor element 10 is suspended above the upper surface of the humidity sensitive layer 20. The separation of the sensor element 10 from the humidity sensitive layer 20 can further reduce heat losses to the substrate 2 during operation. Moreover, because the underside of the sensor element 10 becomes exposed relative to the example described above in relation to FIG. 1, the surface area of the sensor element 10 is increased, in principle therefore increasing the sensitivity of the thermal conductivity based gas sensor.

The integrated circuit shown in FIG. 2, can be constructed using substantially similar methods used for constructing an integrated circuit of the kind shown in FIG. 1. For example, an integrated circuit of the kind shown in FIG. 1 can first be produced and then further processed by removing (by etching) an upper portion 74 of the humidity sensitive layer 20. This has the effect of suspending the sensor element 10 above the new surface of the humidity sensitive layer 20.

Figure 3:
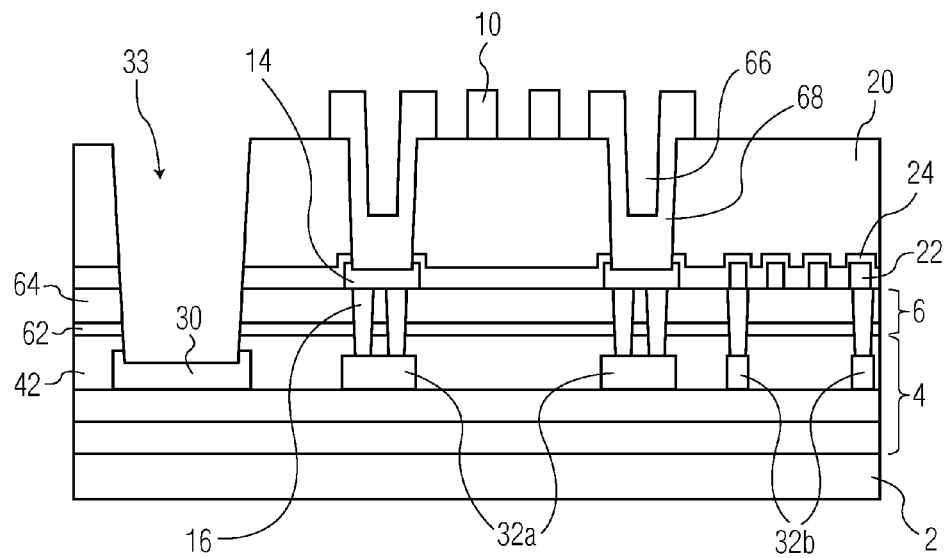
FIG. 3 shows a cross section of an integrated circuit according to a further embodiment of the invention.

FIG. 3 illustrates a further example of an integrated circuit according to embodiment of the invention. The example in FIG. 3 is again similar to that described in relation to FIGS. 1 and 2, and the common features of these embodiments will not be elaborated upon here further. The principle difference between the example in FIG. 3 and the examples described above is that the vias 12 in FIG. 1 are replaced by wider vias 66 that are partially filled with electrically conductive material. In this example, the electrically conductive material 68 within the vias 66 is formed from the same material as that used to form the electrically resistive sensor element 10 of the thermal conductivity based gas sensor. As described in more detail below (see FIG. 7), this allows connection to be made through the humidity sensitive layer 20 with the same metal feature that is used to form the electrically resistive sensor element 10. Potentially, this can reduce the number of process steps required, since the metal used to form the electrically resistive sensor element 10 and to partially fill and coat the side walls of the vias 66 can be laid down in a common process step. It is noted that the metal features 14 on the passivation stack 6 that provide connection between the vias 66 and the vias 16 can be made relatively wide, thereby correctly to receive the relatively wide bases of the vias 66. Additionally, as shown in FIG. 3, more than one via 16 can optionally be provided passing through the passivation stack 6, for each portion of metal 14 above the passivation stack 6.

Figure 4:
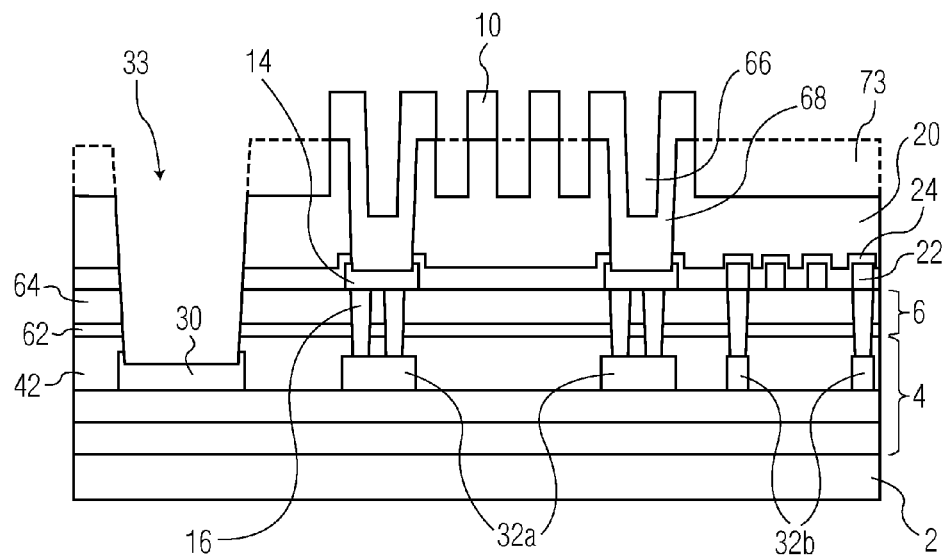
FIG. 4 shows a cross section of an integrated circuit according to another embodiment of the invention.

FIG. 4 illustrates another example of an integrated circuit according to an embodiment of the invention. FIG. 4 is similar to the example described above in relation to FIG. 3. However, in common with the back etching of the humidity sensitive layer 20 described above in relation to FIG. 2, in the example of FIG. 4, the humidity sensitive layer 20 is again back etched to remove at least a portion 72 thereof. This back etching may, in some examples, completely remove the portion of the humidity sensitive layer 20 located immediately beneath the electrically resistive sensor element 10 as described previously in relation to FIG. 2. However, such embodiments may potentially suffer from the problem that the complete removal of the humidity sensitive layer 20 from beneath the electrically resistive sensor element 10 structurally weakens the device to the extent that it may become damaged by mechanical shock either during packaging or after the integrated circuit has entered use.

Accordingly, in the example of FIG. 4, the back etching of the humidity sensitive layer 20 is partial in the sense that only a portion 73 of the humidity sensitive layer 20 is removed. This can be achieved using, for example, a directional back etch, whereby material of the humidity sensitive layer 20 immediately beneath the electrically resistive sensor element 10 is retained. In this way, although the surface area of the sensor element 10 is not increased by the back etch as noted above in relation to FIG. 2, the degree to which heat may be dissipated through the humidity sensitive layer 20 is at least partially limited.

Figure 5:
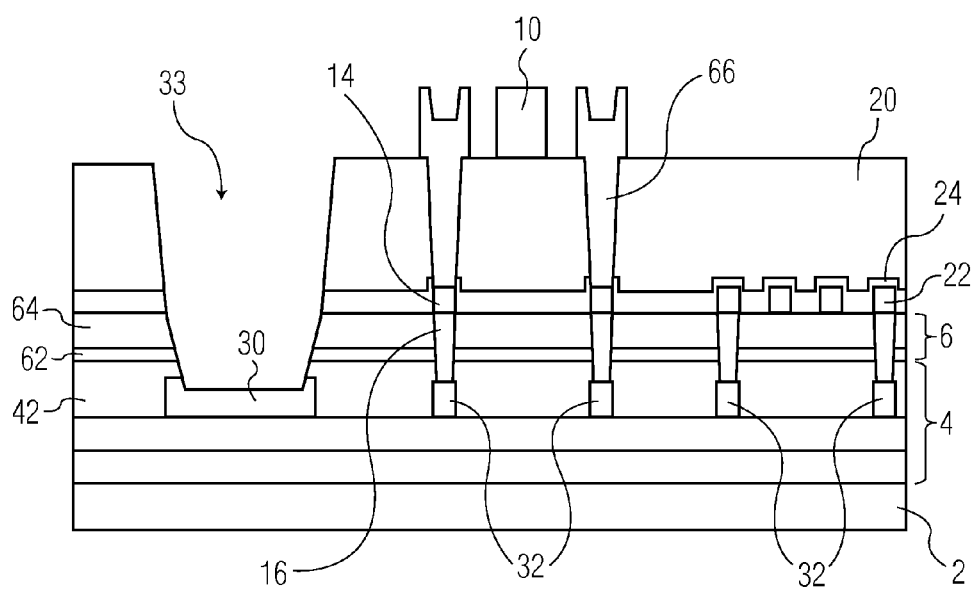
FIG. 5 shows a cross section of an integrated circuit according to a further embodiment of the invention.

FIG. 5 illustrates a further example of an integrated circuit according to an embodiment of the invention. The example in FIG. 5 is similar to the examples described above in relation to FIGS. 1 and 2 in the sense that the vias 66 passing through the humidity sensitive layer 20 are completely filled. However, in common with the example of FIGS. 3 and 4, the material used to fill the vias 66 is the same material as that used to form the sensor element 10. In common with the examples of FIGS. 3 and 4 therefore, the vias 66 can be filled at the same time and in the same process step as that used to form the sensor element 10. This will be described in further below (see FIG. 8).

In all of the examples described above, it is clear that embodiments of the invention can allow the relative humidity sensor and the thermal conductivity based gas sensor to be placed relatively close together on a single semiconductor substrate, yielding benefits relating to the greater accuracy with which the corrections for cross-sensitivity of the gas sensor to humidity can be applied. In some embodiments, and as illustrated above in relation to FIGS. 1 to 5, to gain the maximum benefit of the close proximity of the two sensors, the relative humidity sensor and the thermal conductivity based gas sensor can be located adjacent each other on the substrate. For the purposes of the present application, the term "adjacent" means that the two sensors are provided on the substrate without any intervening components.

As noted above, thermal conductivity based gas sensors can also suffer from cross-sensitivity to ambient temperature. In accordance with an embodiment of the invention, the integrated circuit can be provided also with a temperature sensor for correcting for this additional cross-sensitivity. The temperature sensor can be conventional in nature. In some embodiments, a plurality of environmental sensors including a relative humidity sensor, a thermal conductivity based gas sensor, a temperature sensor and at least one further kind of sensor (for example a pressure sensor and/or a flow sensor) can be provided on the same semiconductor substrate in a single package. This allows multi-modal sensing functionality in a single substrate which can be mass produced at low cost and which can be packaged in a manner particularly suitable for applications such as those noted below.

An integrated circuit of the kind described herein, can, for example, be incorporated into a radio frequency identification (RFID) tag. The sensor can be connected to circuitry of the RFID tag, including features such as an antenna to allow readout of sensing data collected by the sensor. Similarly, an integrated circuit of the kind described herein, may be incorporated into a mobile communications device such as a laptop, tablet or mobile telephone to allow the device to collect data relating to the presence of a target gas and use the data for various applications.

It is further envisaged that an integrated circuit of the kind described herein, could be incorporated into a heating, ventilation and air conditioning (HVAC) system. This would allow the HVAC system to collect information relating to the presence of one or more target gasses in the heating, ventilation or air conditioning of, for example, a building (for example a greenhouse or office building), or a vehicle such as an automobile or an aircraft.

FIGS. 6A to 6L schematically illustrate a method of making an integrated circuit according to an embodiment of the invention. In particular, the process steps described below in relation to FIGS. 6A to 6L are suitable for forming an integrated circuit of the kind described above in relation to FIGS. 1 and 2.

Figure 6A:
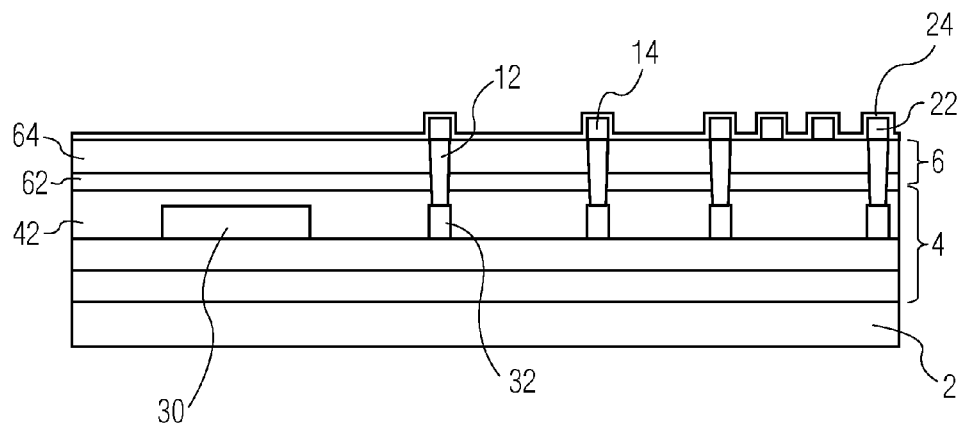
FIGS. 6A to 6L show cross sections of an integrated circuit which illustrate a number of process steps for making an integrated circuit of the kind shown in FIGS. 1 and 2.

A first step in the manufacture of an integrated circuit according to the present embodiment is illustrated in FIG. 6A. In this step, there is provided a semiconductor substrate 2. The substrate 2 can include features such as control circuitry, ADCs and memory for storing readings or other data as noted above. These features can be formed in the substrate 2 using standard front end of line (FEOL) processing steps.

The substrate 2 is provided with a metallization stack 4 upon which there is further provided a passivation stack 6. The metallization stack 4 and the passivation stack 6 can be substantially as described above in relation to FIG. 1, and can be formed using standard BEOL processing steps. Steps of this kind are well-known in the art and will not be elaborated upon further herein.

When forming the metallization stack 4 and the passivation stack 6, provision can be made for making connection to the relative humidity sensor and thermal conductivity based gas sensor that will subsequently be formed above the passivation stack. Accordingly therefore, one of the upper metal levels 42 in the metallization stack 4 may be provided with metal features 32 for connecting the sensors with the stack 4.

Furthermore, in the present embodiment, vias 12 can be formed through the passivation stack 6 to connect to the metal features 32 in the metal level 42 of the metallization stack 4. These vias 12, which are filled with electrically conductive material, can be formed using standard lithographic and etching processes and can be filled using standard metal deposition techniques.

After the vias 12 have been filled, metal features can be formed above the passivation stack 6. In the present example, the metal features 22 are formed directly on the passivation stack 6, however in other examples there may be one or more intervening layers.

The metal features can include metal features 14 that will connect subsequently to the sensor element of the thermal conductivity based gas sensor. Also, in the same step, the sensor electrodes 22 of the relative humidity sensor can be formed. The electrodes 22 can, as shown in FIG. 6A, be configured as a pair of interdigitated sets of fingers, to increase their surface area. The metal features 14 and the electrode pair 22 can be formed using BEOL process steps involving standard lithographic and etching techniques to pattern a deposited metal layer into the desired configuration.

The metal features 14 and the electrode pair 22 can next be protected from corrosion with the deposition of a corrosion protection layer 24 comprising, for example, $Ta_5O_2$.

Figure 6B:
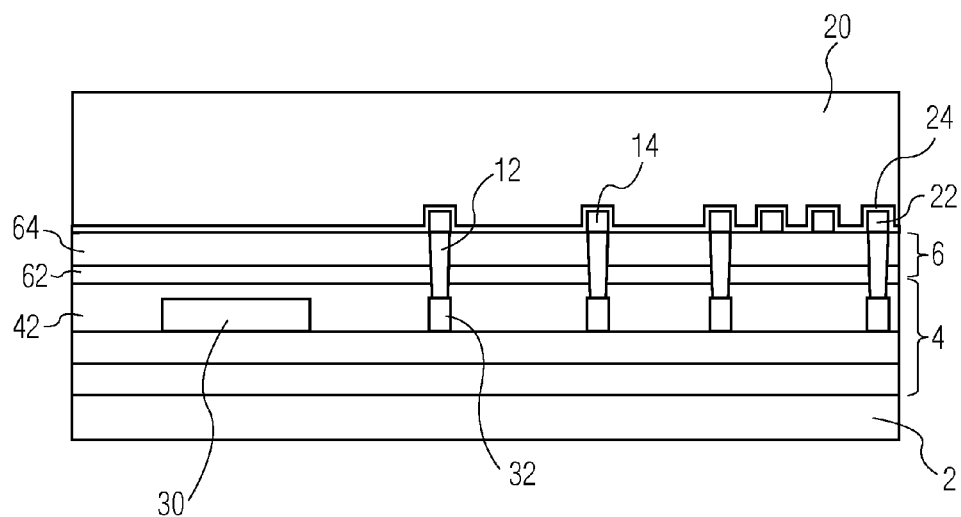

Following the above described processing, a next stage in the manufacture of the integrated circuit is illustrated in FIG. 6B. In this step, a layer 20 of humidity sensitive material is deposited over the substrate to cover the sensor electrodes 22 and the other features that are exposed above the passivation stack 6. The layer 20 of humidity sensitive material can, for example, comprise polyimide of any of the alternative materials noted above. In some embodiments, the humidity sensitive material can be flood exposed on to the substrate (i.e. full wafer exposure without the provision of any kind of mask) and then cured.

Figure 6C:
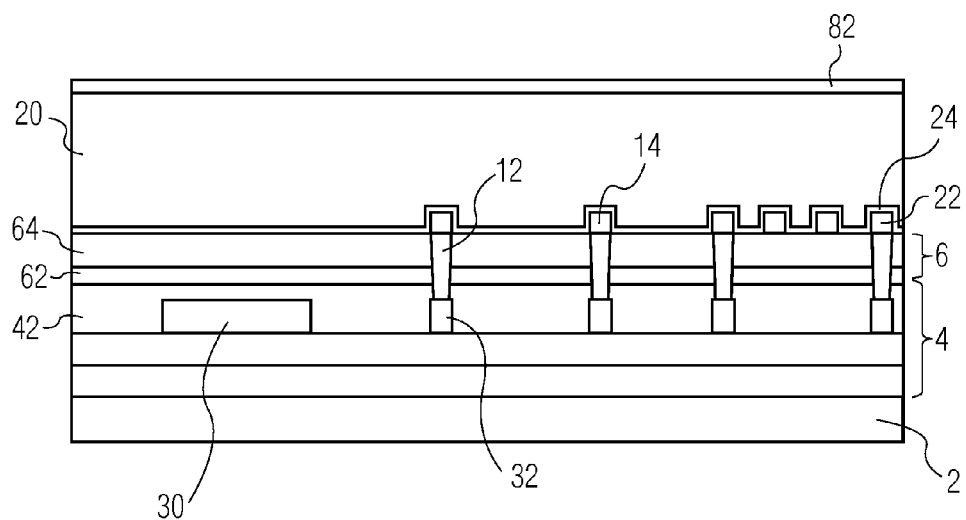
Figure 6D:
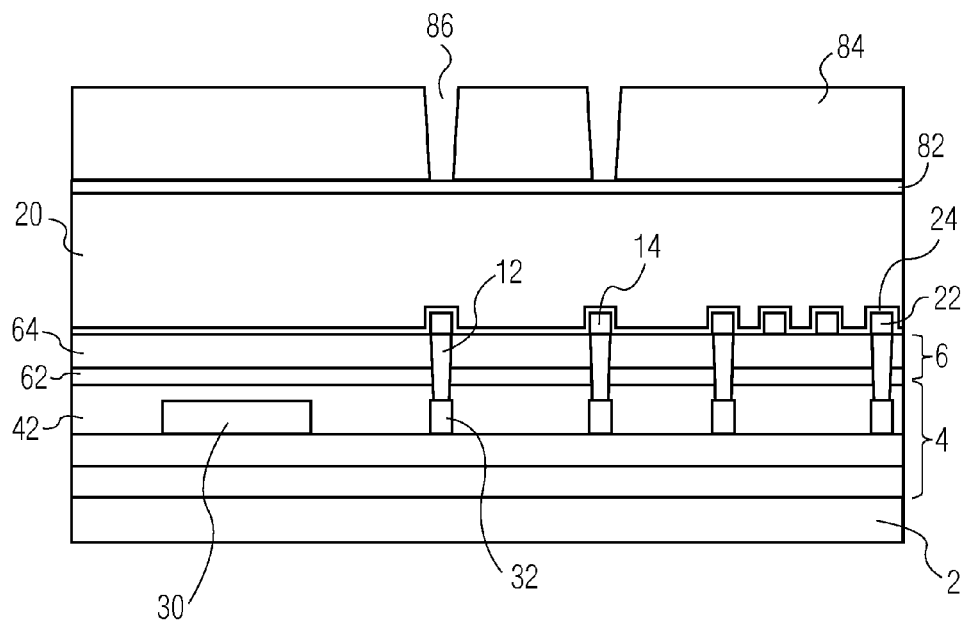
Figure 6E:
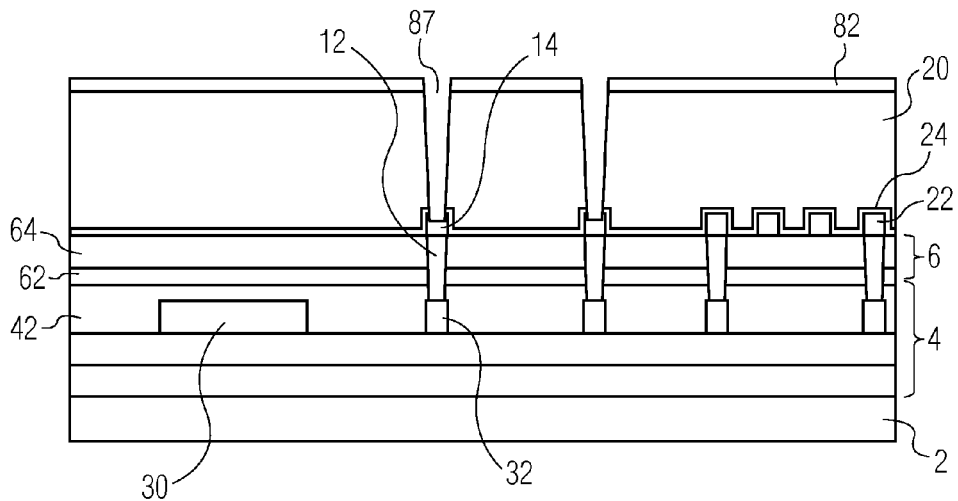

In a next step illustrated in FIG. 6C, a layer of oxide 82 can be deposited over the humidity sensitive layer 20. Thereafter, as shown in FIG. 6D, a mask 84 can be deposited on to the oxide layer 82 and then patterned to produce openings 86 through which a subsequent etching process can, after removal of the mask 84, produce the structure shown in FIG. 6E. Note that the etching process also removes an upper portion of the corrosion protection layer 24 at the metal features 14, thereby to allow electrical connection of those metal portions 14 to the resistive sensor element of the thermal conductivity based gas sensor.

Figure 6F:
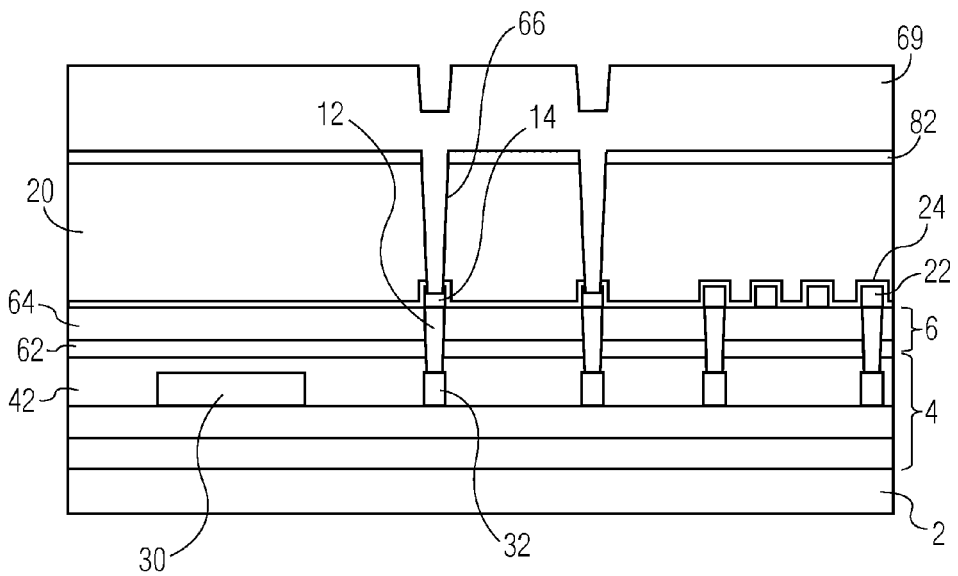
Figure 6G:
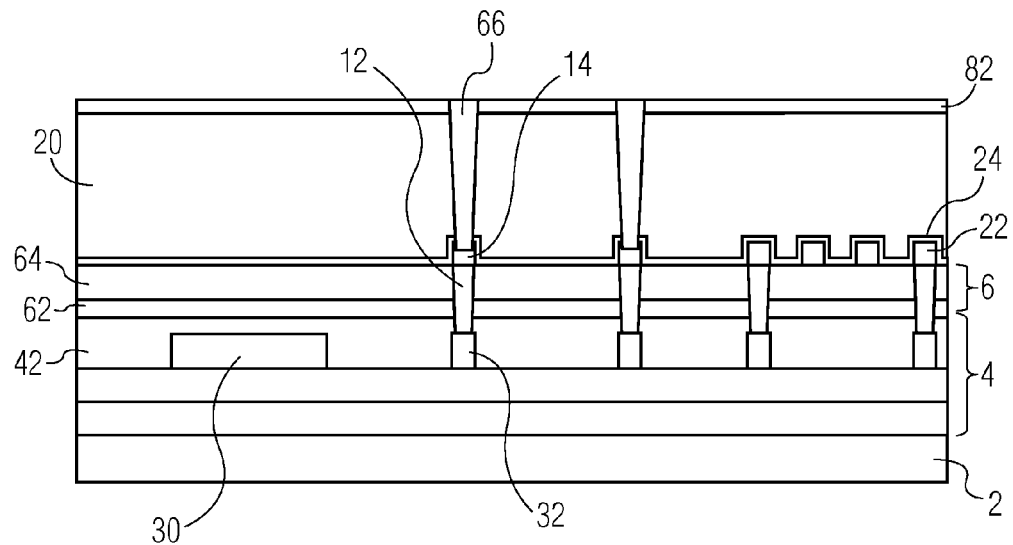

Following removal of the mask 84, as shown in FIG. 6F, a next step involves depositing a metal (e.g. aluminium, tungsten, an AlCu alloy, or some other BEOL process compatible material) over the substrate so as to fill the vias to produce vias 66 through the humidity sensitive layer 20 forming electrical connections to the metal features 14. In some examples, a liner comprising a material such as TiN or Ti/TiN can be deposited prior to deposition of the metal. The liner can act as an adhesion layer for the metal. The excess metal 69 outside the vias 66 (including any liner that is used) can then be removed to produce the structure showing in FIG. 6G.

Figure 6H:
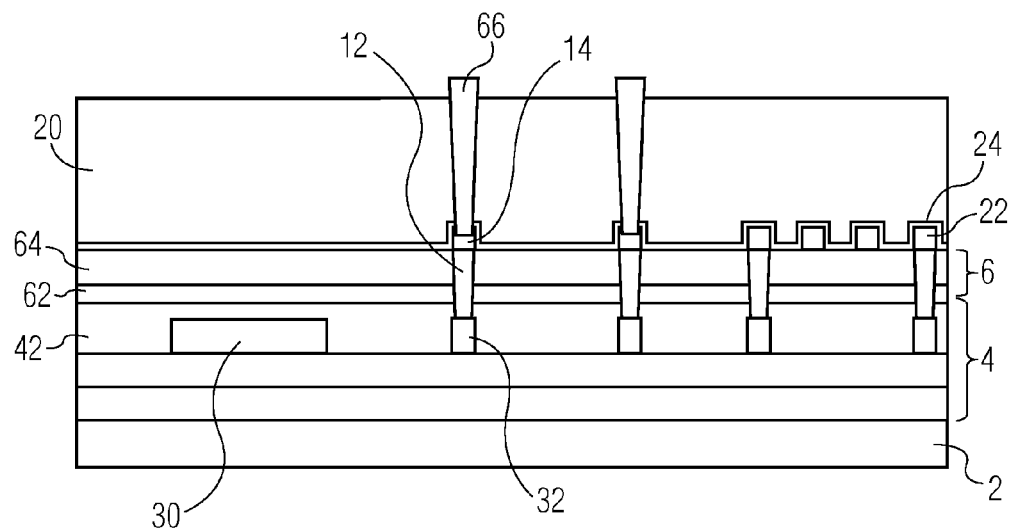

After removal of the excess metal, the oxide layer 82 can also be removed (e.g. by wet or dry etch), leading to the structure showing in FIG. 6H. As can be seen in FIG. 6H, removal of the oxide layer 82 leads to the slight protrusion of the metal contained in the vias 66 above the surface of the humidity sensitive layer 20. This protrusion can potentially be removed, but may also be beneficial in the sense that it can increase the robustness of the contact between the metal in the vias 66 and the ends of the electrically resistive sensor element 10 that will subsequently be formed.

Figure 6I:
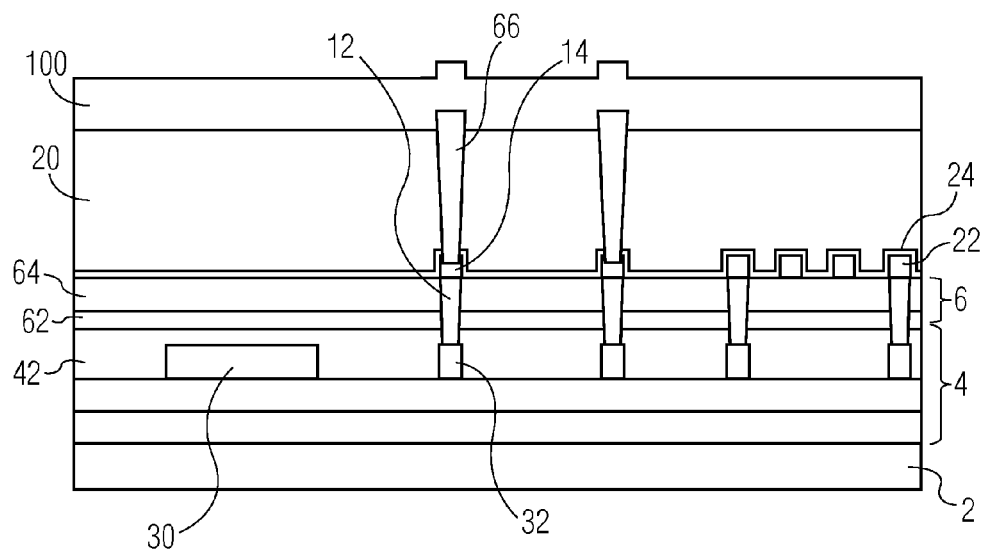

A next step in the method of manufacturing the integrated circuit is illustrated in FIG. 6I. In this step, a layer of material 100 is deposited over the humidity sensitive layer 20. This material will subsequently form the electrically resistive sensor element of the thermal conductivity based gas sensor. Accordingly, the material in the layer 100 is typically and electrically resistive material such as aluminium or tungsten. Similar to the step described above in relation to FIG. 6F, a liner comprising a material such as TiN or Ti/TiN can be deposited prior to deposition of the material 100. Again, the liner can act as an adhesion layer.

Figure 6J:
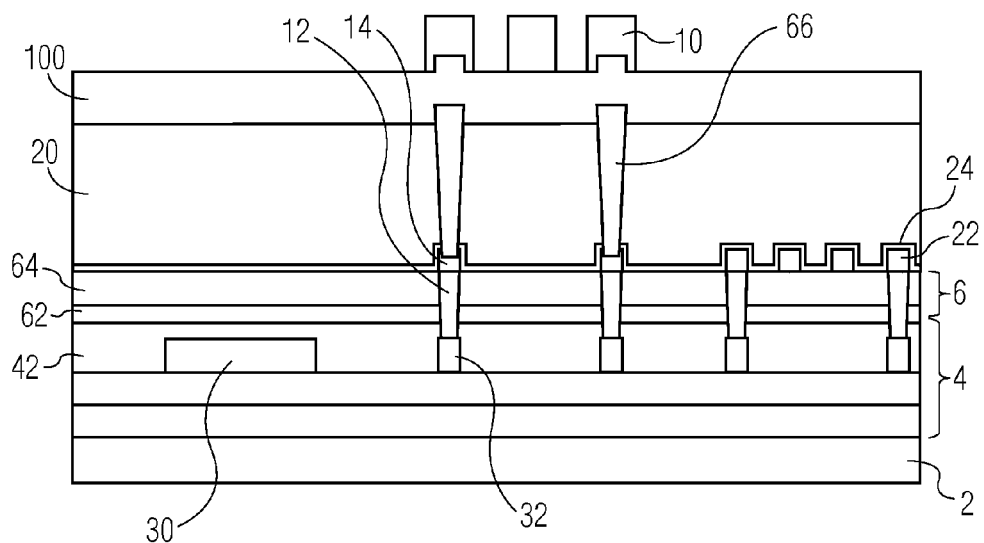
Figure 6K:
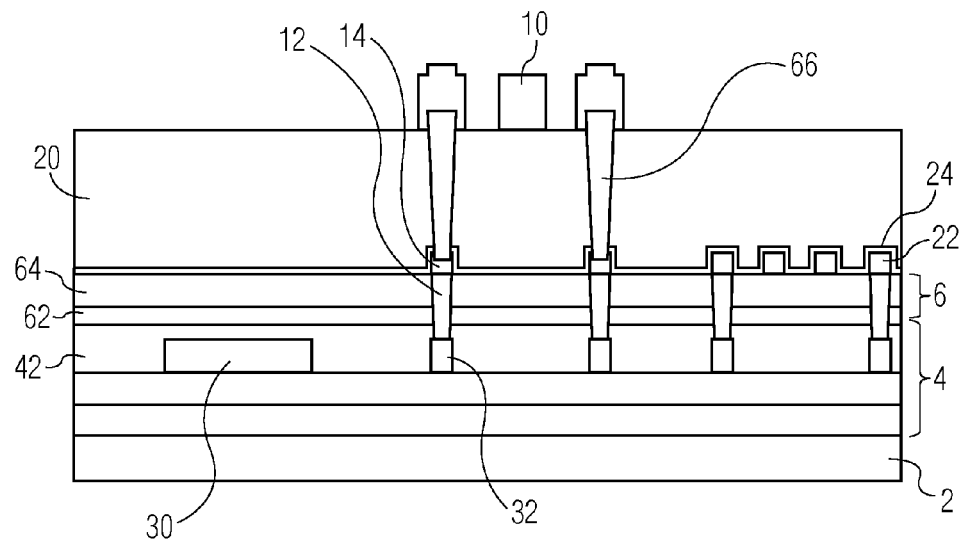

Following deposition of the layer 100, a mask 110 is laid down using standard lithographic techniques (see FIG. 6J). Following the provision of the mask 110, an etching step can be used to remove those parts of the layer 100 that remain exposed (plus the liner, if used), leading to the structure shown in FIG. 6K. As can be seen in FIG. 6K, the remaining parts of the layer 100 form the electrically resistive sensor element 10 of a thermal conductivity based gas sensor, which is located above the humidity sensitive layer 20.

The configuration and layout of the sensor element 10 can be tailored by choosing the appropriate configuration for the mask 110. In the present example, the sensor element 10 is laid out in a meander configuration as is well-known in the art. However, other configurations could be employed in accordance with design requirements.

Figure 6L:
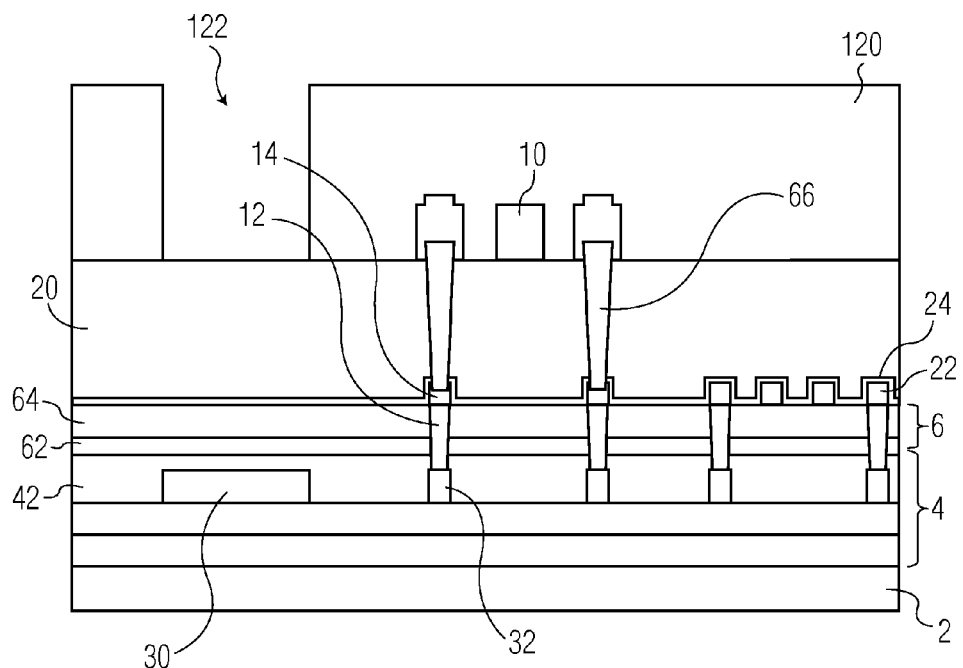

After the sensor element 10 has been formed, as shown in FIG. 6L, a further mask 120 can be laid down and patterned to produce an opening 122 therein. This opening 122 can allow a further etching step to produce an opening 33 of the kind described above in relation to FIGS. 1 and 2 for allowing access to the bond pad 30 in the integrated circuit. Following subsequent removal of the further mask 120, the structure shown in FIG. 1 is reached.

As already described above, at this stage the electrically resistive sensor element 10 is located on an upper surface of the humidity sensitive layer 20. However, as shown in FIG. 2, an optional further step can now be used to remove a portion 74 of the humidity sensitive layer 20, whereby the sensor element 10 becomes suspended above the surface of the remaining part of the humidity sensitive layer 20.

When removing the part 74 (FIG. 2) of the humidity sensitive layer 20, it has been found that it is preferable to ensure that the thickness of the remaining part of the humidity sensitive layer 20 remains larger than around 2 microns. If the remaining part of the humidity sensitive layer 20 is too thin, the relative humidity sensor may lose sensitivity to the extent that normal function becomes difficult.

A further embodiment of a method of making an integrated circuit will now be described with reference to FIG. 7. The process steps illustrated in FIGS. 7A to 7G are suitable for making an integrated of the kind discussed herein above in relation to FIGS. 3 and 4.

Figure 7A:
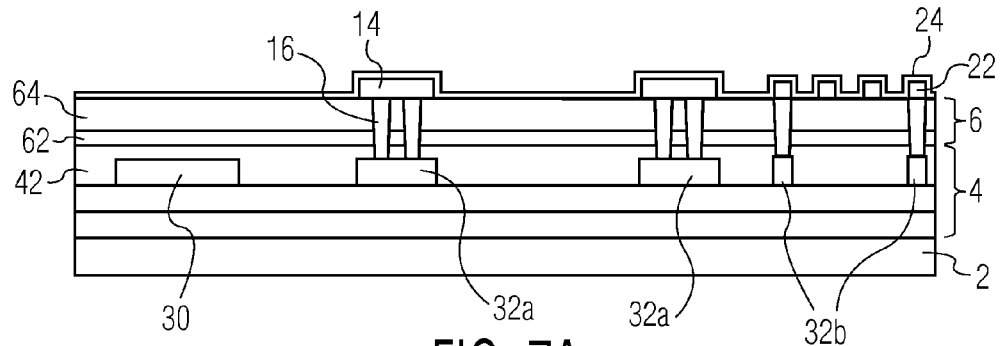
FIGS. 7A to 7G show cross sections of an integrated circuit which illustrate a number of process steps for making an integrated circuit of the kind shown in FIGS. 3 and 4.

In a first step shown in FIG. 7A, there is provided a semiconductor substrate 2 having thereon a metallization stack 4 covered with a passivation stack 6. The substrate 2, metallization stack 4 and passivation stack 6 can be formed substantially as already described herein above.

An upper layer 42 of the metallization stack 4 includes metal features 32A and 32B as well as a bond pad 30 which will later be exposed for electrical connection to the integrated circuit. Again, the metal features 32B form connections for the relative humidity sensor, whereas the metal features 32A form connections for the thermal connectivity based gas sensor.

It will be noted that in contrast to the arrangement in FIG. 6, the metal features 32A in the present example are somewhat wider. Also as shown in FIG. 7A, a series of vias 16 pass through the passivation stack 6 to connect the metal features 32A and 32B to the sensors of the integrated circuit. Since the metal features 32A are somewhat wider, more than one such via 16 can be provided therefor. In the present example, two such vias 16 are provided per metal feature 32A.

As already described above in relation to FIG. 6A, above the passivation stack 6 there can be provided a number of further metal features such as the first and second sensor electrodes 22 of the relative humidity sensor. Also, in the same layer, metal features 14 can be provided to allow connection to vias 66 passing through the humidity sensitive layer 20 that will subsequently be deposited. As also noted above, the features on the passivation stack 6 can be coated at this stage with a corrosion protection layer 24.

Figure 7B:
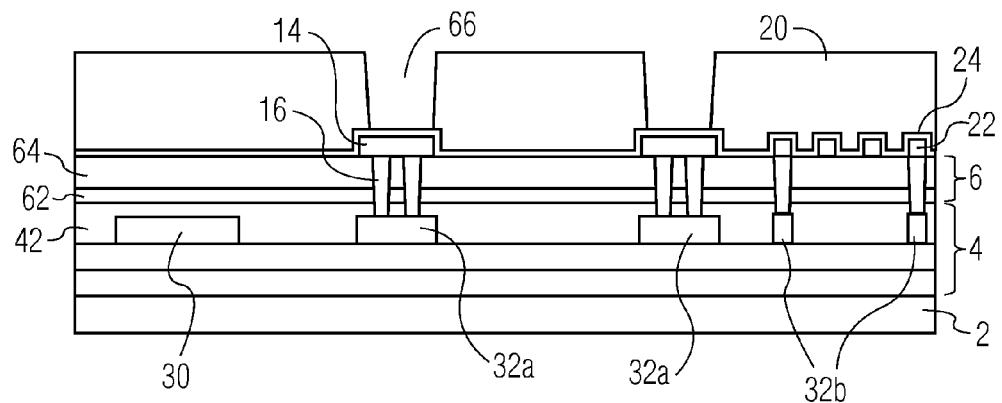
Figure 7C:
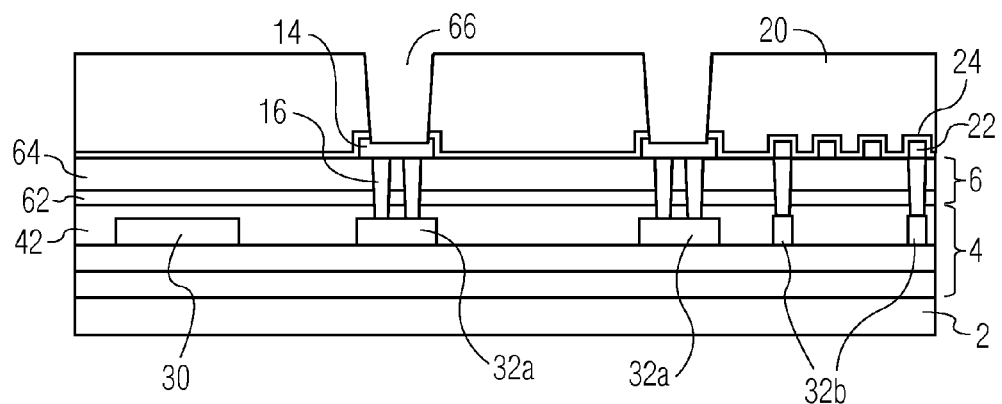

A next step in the process is illustrated in FIG. 7B. In this step, a humidity sensitive layer 20 is deposited on to the substrate 2 and then patterned to produce vias 66. The vias 66 in this example are relatively wide. In the present example, the etching step which produces the vias 66 does not affect the corrosion protection layer 24. Accordingly therefore, as shown in FIG. 7C, a second etching step can be applied (such as a metal dry etch), for removing the portion of the corrosion protection layer 24 which lies at the bottom of the vias 66, thereby to expose the metal portions 14.

Figure 7D:
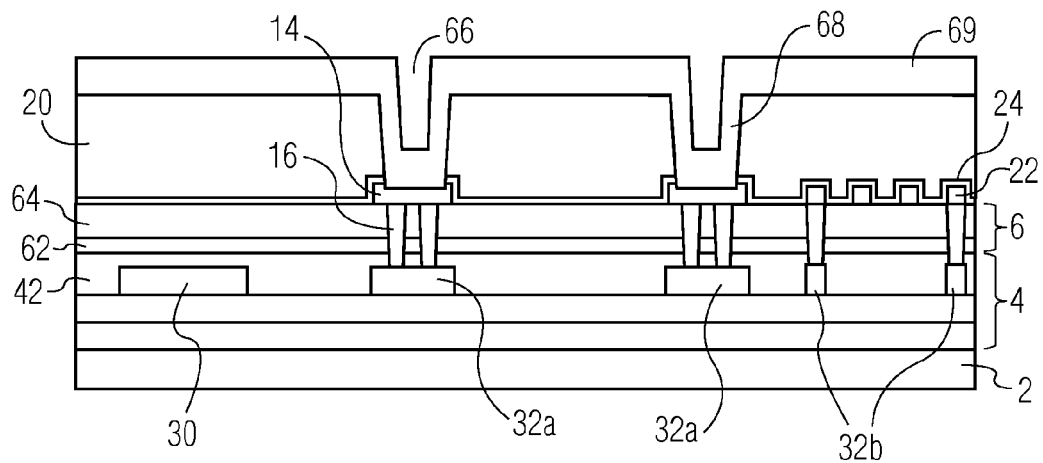

Next, as shown in FIG. 7D, a metal layer 69 is deposited over the humidity sensitive layer 20, thereby to cover the humidity sensitive layer 20 and to at least partially fill the vias 66. As shown in FIG. 7D, the parts 68 of the layer 69 in the vias 66 only partially fill the vias 66 in the present example, thereby to coat the side walls of the vias 66. In this way, the material for the sensor element 10 and for the connections between the sensor element and the metal portions 14 can be deposited in a common process step. This is in contrast to the example described above in relation to FIG. 6, in which separate metal deposition steps are required to produce the metal filled vias 66 and the sensor element 10.

Figure 7E:
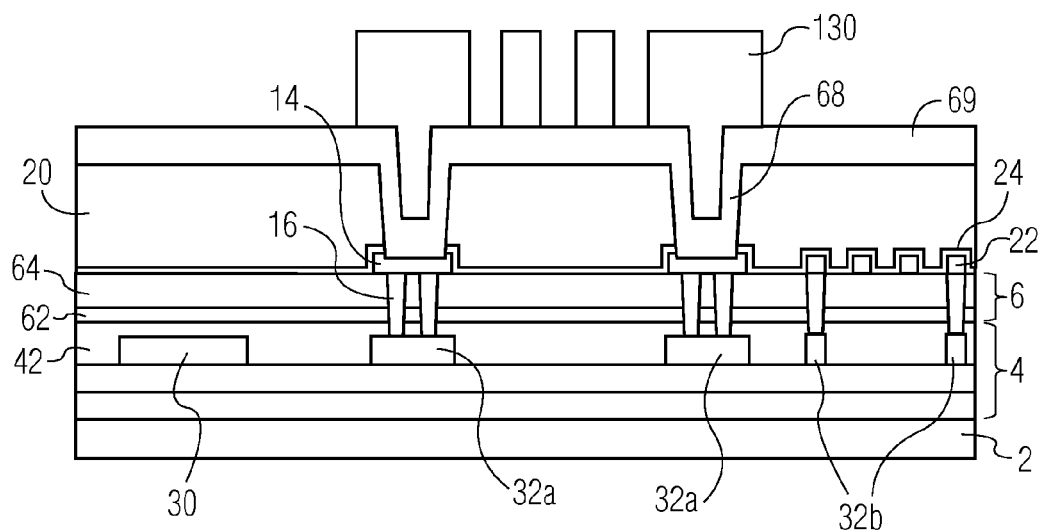
Figure 7F:
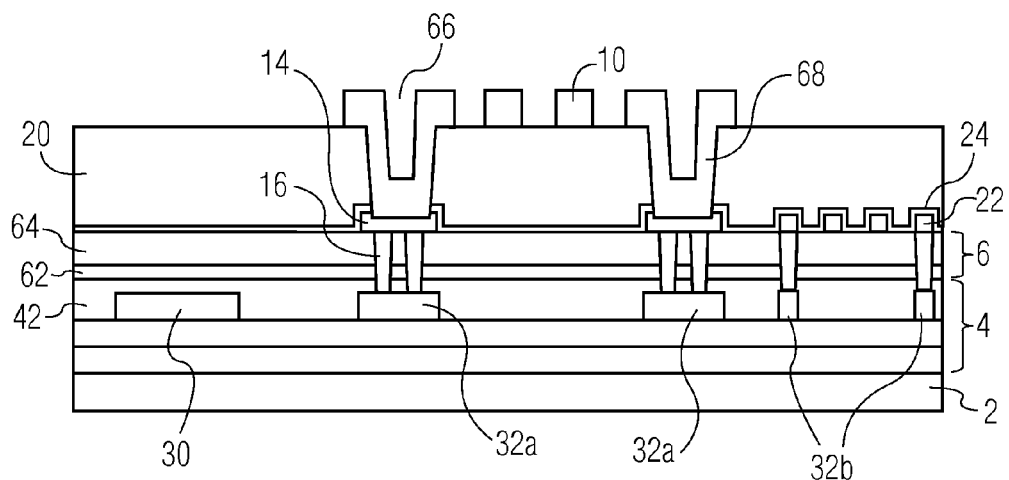
Figure 7G:
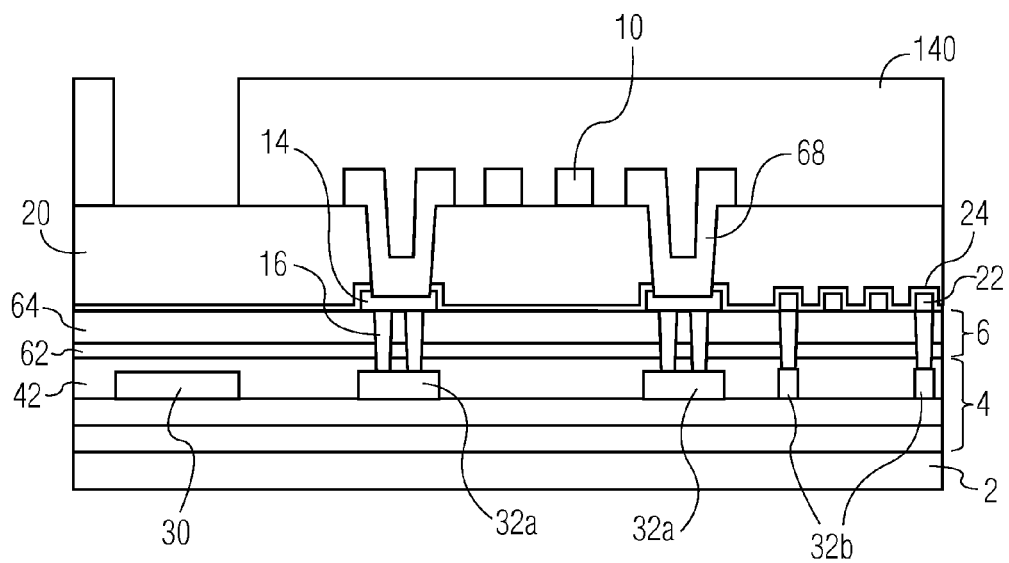

A next step as shown in FIG. 7E, the layer 69 can be patterned to produce the desired configuration of the resistive sensor element 10 of the thermal conductivity based gas sensor. To pattern the layer 69, a mask 130 is laid down on the layer 69 and then patterned in the appropriate way. Following the laying down of the mask 130, standard etching techniques can be used and the mask 130 can subsequently be removed, thereby to produce the arrangement shown in FIG. 7F. As noted elsewhere herein, the sensor element 10 may be provided in a meander pattern configuration, which is shown in FIG. 7 in cross section.

To complete the integrated circuit, a further mask 140 can be laid down over the humidity sensitive layer 20 and sensor element 10, and then patterned to allow an opening 33 of the kind described above in relation to FIGS. 3 and 4 to be made exposing the bond pad 30. The arrangement of FIG. 3 is reached following subsequent removal of the mask 140. Again, as described above, an optional further processing step can be employed to remove a portion 72 (FIG. 4) of the humidity sensitive layer 20, thereby further to reduce heat losses to the substrate 2 during operation.

A further process for making an integrated circuit in accordance with an embodiment of the invention is illustrated in FIGS. 8A to 8H. In particular, the process described below is suitable for making an integrated circuit of the kind illustrated in FIG. 5. The initial stages of the process (FIGS. 8A and 8B) are substantially similar to those already described above in relation to FIGS. 6A, 6B and 7A and 7B. It will be noted though with comparison of FIGS. 6, 7 and 8, that in the example of FIG. 8, the metal portions 14 are not as wide as those described in relation to FIG. 7 and can be substantially similar to those described in FIG. 6.

Figure 8A:
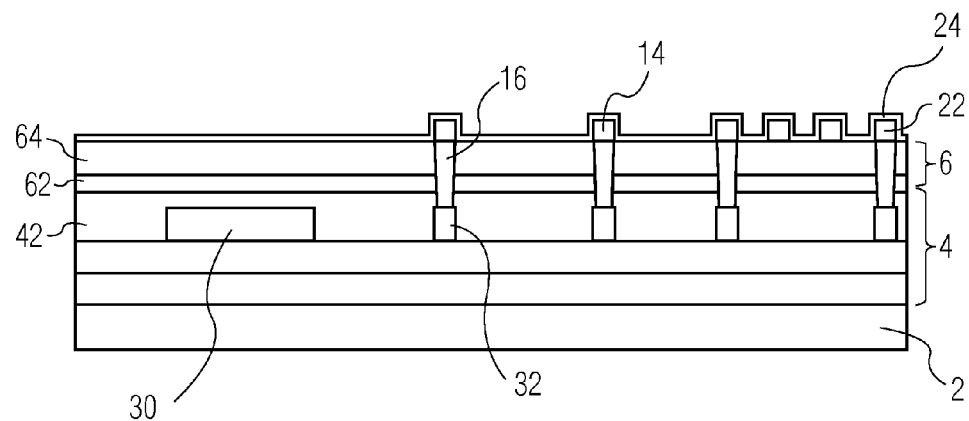
FIGS. 8A to 8H show cross sections of an integrated circuit which illustrate a number of process steps for making an integrated circuit of the kind shown in FIG. 5.
Figure 8B:
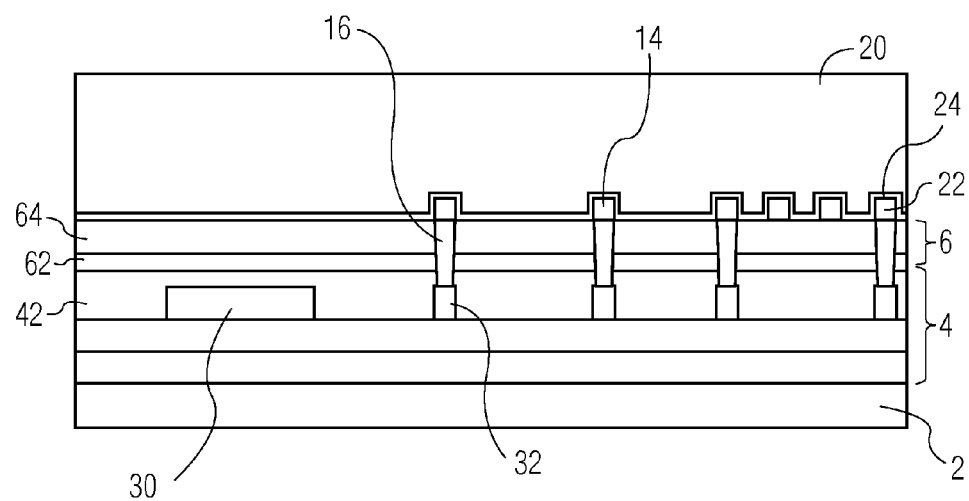
Figure 8C:
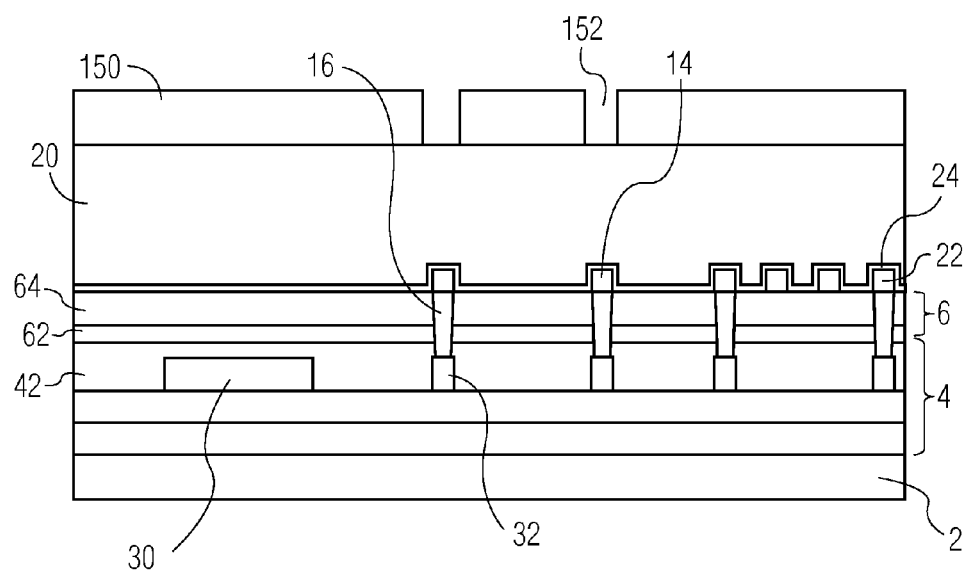

Following the deposition of the humidity sensitive layer 20 (FIG. 8B), a mask 150 is laid down on to an upper surface of the humidity sensitive layer 20 and then patterned to produce openings 152 as shown in FIG. 8C. An etching process is then used to etch through the openings 152 in the mask 150 to produce vias 67 passing through the humidity sensitive layer 20 and the corrosion protection layer 24. This etching process may include separate etching steps for etching away the humidity sensitive layer 20 and the upper portions of the corrosion protection layer 24 to reveal the metal features 14 located on the upper surface of the passivation stack 6. As noted above, in some examples this could alternatively be achieved with a single etching step.

Figure 8D:
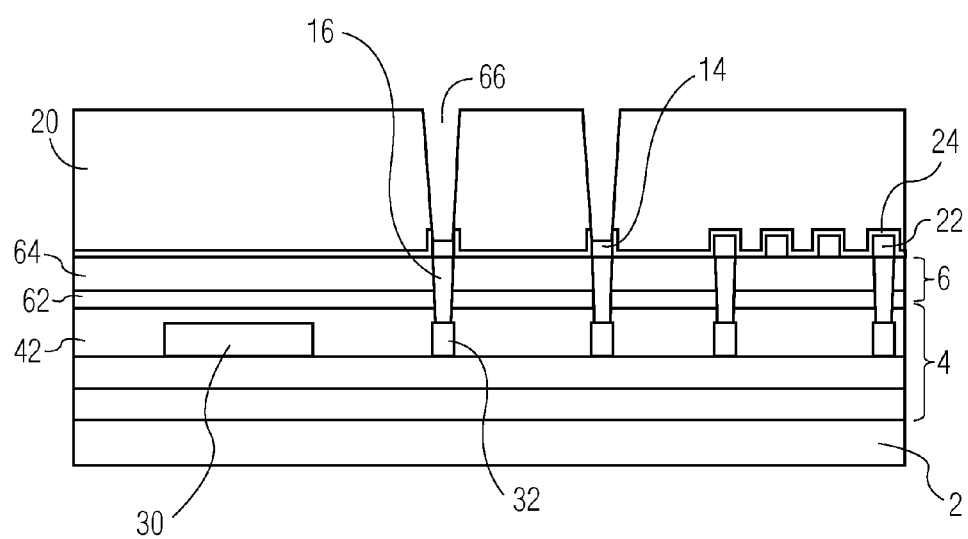
Figure 8E:
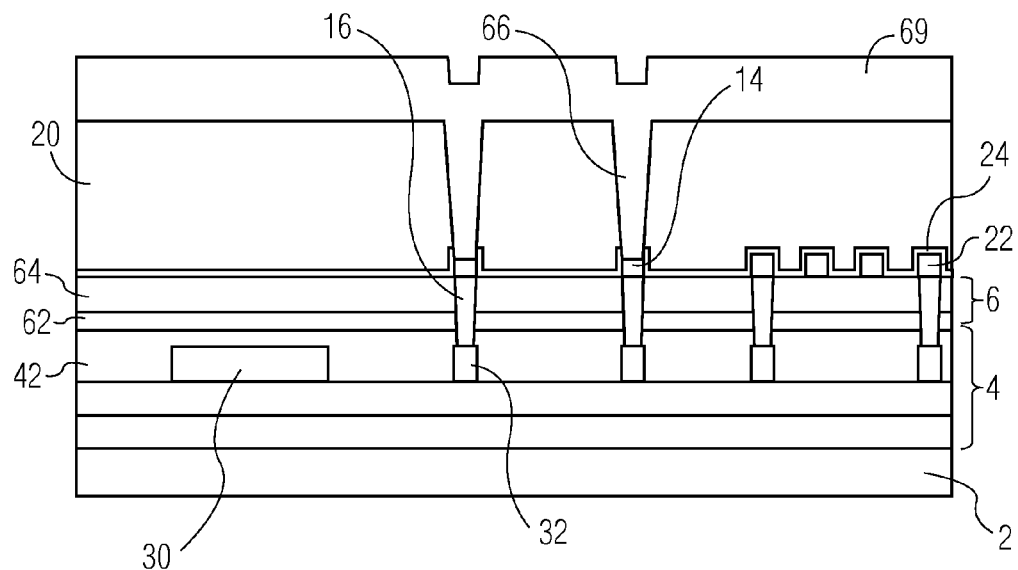
Figure 8F:
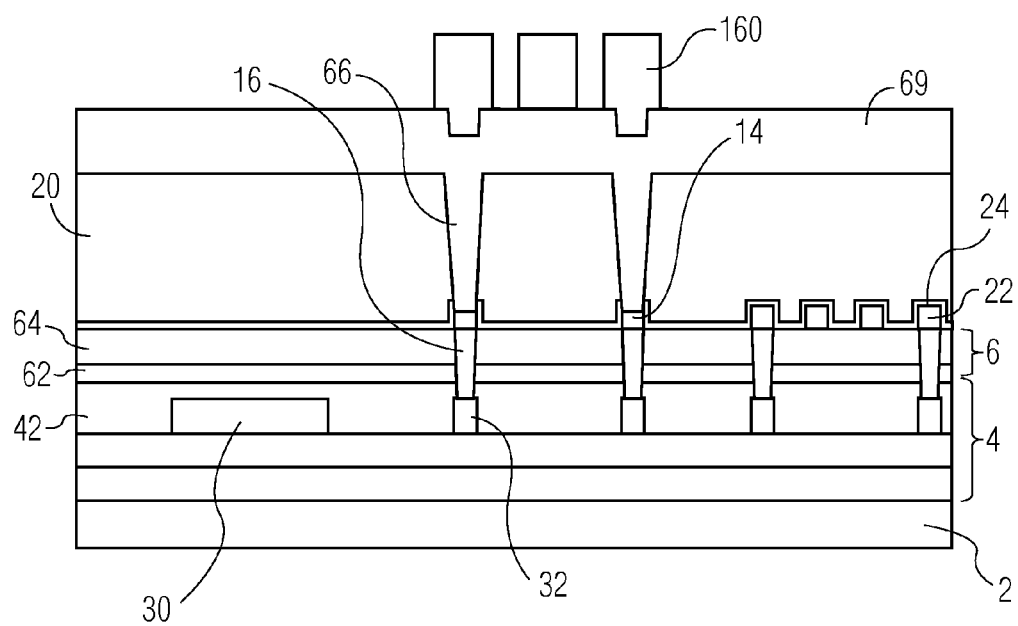

After subsequent removal of the mask 150, the structure of FIG. 8D is reached. Thereafter, as shown in FIG. 8E, a metal layer 69 can be deposited to cover the humidity sensitive layer 20 and to fill the vias 66. Accordingly, although the vias 66 in the present example are narrow as in FIG. 6, the metal deposition step for filling the vias 66 and for laying down the required material 69 for the electrically resistive sensor element 10 of the thermal conductivity based gas sensor can be achieved in a single deposition step.

Figure 8G:
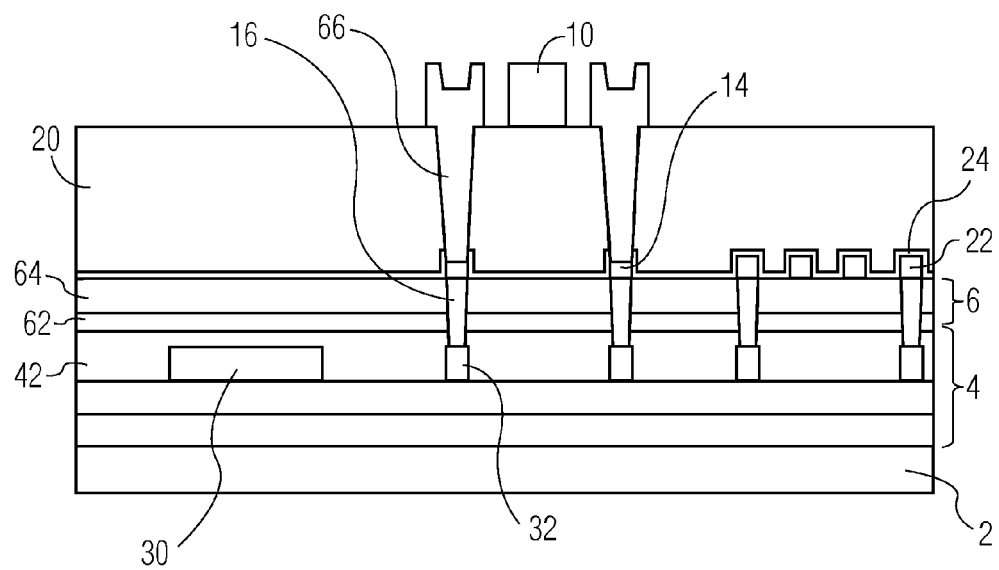

After the deposition of the layer 69, a mask 160 can be deposited and patterned (FIG. 8F) and a subsequent etching process can be used to produce the structure shown in FIG. 8G, including the electrically resistive sensor element 10 of the thermal conductivity based gas sensor.

Figure 8H:
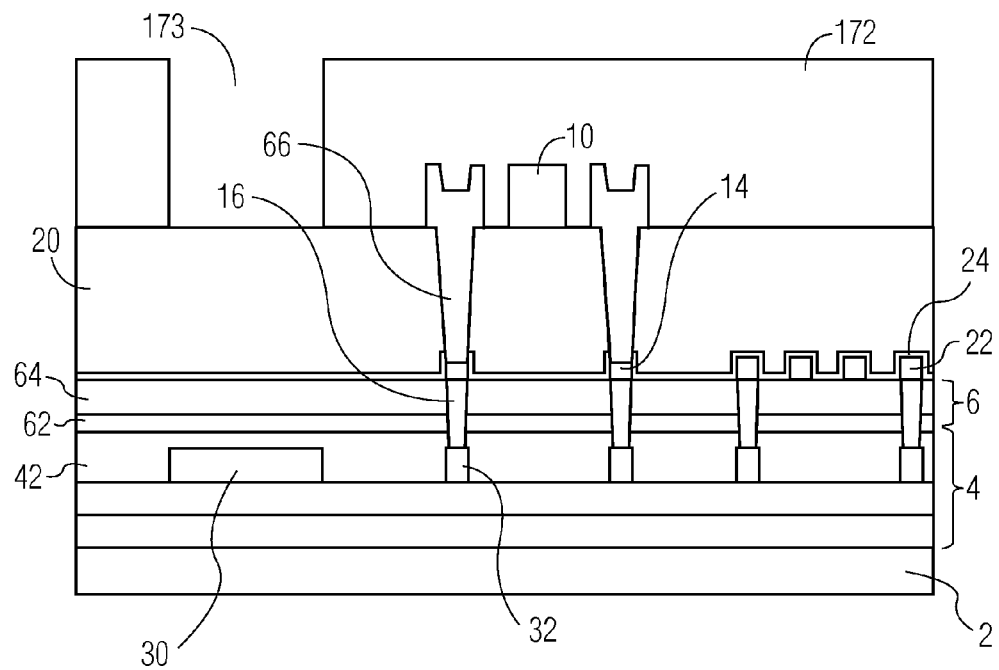

Finally, as shown in FIG. 8H, a further mask 172 can be deposited over the humidity sensitive layer and sensor element 10 and then patterned to produce and opening 173 through which an opening 33 of the kind illustrated in FIG. 5 can be made for access to the bond pad 30. Following removal of the mask 172, the structure of FIG. 5 is reached.

Accordingly, there has been described an integrated circuit and a method of making the same. The integrated circuit includes a semiconductor substrate. The integrated circuit also includes a relative humidity sensor on the substrate. The relative humidity sensor includes a first sensor electrode, a second sensor electrode, and a humidity sensitive layer covering the first and second electrodes. The integrated circuit further includes a thermal conductivity based gas sensor. The thermal conductivity based gas sensor has an electrically resistive sensor element located above the humidity sensitive layer.

Although particular embodiments of the invention have been described, it will be appreciated that many modifications/additions and/or substitutions may be made within the scope of the claimed invention.

The invention claimed is:

1. An integrated circuit comprising:
   a semiconductor substrate;
   a relative humidity sensor on the substrate, the relative humidity sensor comprising a first sensor electrode, a second sensor electrode, and a humidity sensitive layer covering the first and second electrodes; and
   a thermal conductivity based gas sensor on the substrate, the gas sensor having an electrically resistive sensor element located above the humidity sensitive layer,
   wherein the electrically resistive sensor element is located on an upper surface of the humidity sensitive layer.

2. The integrated circuit of claim 1 comprising vias passing through the humidity sensitive layer, wherein the vias contain electrically conductive material connecting to the electrically resistive sensor element of the thermal conductivity based gas sensor.

3. The integrated circuit of claim 2, wherein the electrically conductive material in the vias partially fills and coats sidewalls of the vias.

4. The integrated circuit of claim 1 comprising a metallization stack on a major surface of the substrate and a passivation stack on the metallization stack, wherein relative humidity sensor and the thermal conductivity based gas sensor are both located above the passivation stack.

5. The integrated circuit of claim 4 comprising vias passing through the passivation stack, wherein the vias are filled with electrically conductive material connecting the metallization stack to at least one of the electrically resistive sensor element and the first and second sensor electrodes of the relative humidity sensor.

6. The integrated circuit of claim 4 comprising an opening through the humidity sensitive layer and the passivation stack for providing access to a bond pad in the metallization stack for making electrical connection to the integrated circuit.

7. The integrated circuit of claim 1, wherein the thermal conductivity based gas sensor is located adjacent the relative humidity sensor on the substrate.

8. The integrated circuit of claim 1, wherein the electrically resistive sensor element of the thermal conductivity based gas sensor extends in a plane parallel to a major surface of the substrate.

9. The integrated circuit of claim 1 further comprising:
   a temperature sensor, and
   at least one further type of sensor.

10. A Radio Frequency Identification (RFID) tag comprising the integrated circuit of claim 1.

11. A mobile communications device comprising the integrated circuit of claim 1.

12. A heating, ventilation and air conditioning (HVAC) system comprising one or more integrated circuits according to claim 1.

13. A method of making an integrated circuit, the method comprising:
   providing a semiconductor substrate;
   forming a relative humidity sensor on the substrate by forming a first sensor electrode and a second sensor electrode, and then depositing a humidity sensitive layer to cover the first and second electrodes; and
   forming a thermal conductivity based gas sensor on the substrate by forming an electrically resistive sensor element above the humidity sensitive layer of the relative humidity sensor and locating the electrically resistive sensor element on an upper surface of the humidity sensitive layer.

* * * * *